United States Patent
Rosales et al.

(10) Patent No.: US 7,550,497 B2
(45) Date of Patent: Jun. 23, 2009

(54) PHOSPHORAMIDE DERIVATIVES

(75) Inventors: Carmen Almansa Rosales, Barcelona (ES); Javier Bartroli Orpi, Barcelona (ES)

(73) Assignee: Palau Pharma, S.A., Palau-solita i Plegamans (ES)

( * ) Notice: Subject to any disclaimer, the term of this patent is extended or adjusted under 35 U.S.C. 154(b) by 226 days.

(21) Appl. No.: 10/540,490

(22) PCT Filed: Dec. 23, 2003

(86) PCT No.: PCT/EP03/14818

§ 371 (c)(1),
(2), (4) Date: Jan. 20, 2006

(87) PCT Pub. No.: WO2004/058778

PCT Pub. Date: Jul. 15, 2004

(65) Prior Publication Data

US 2006/0111326 A1     May 25, 2006

(30) Foreign Application Priority Data

Dec. 24, 2002    (ES)   ................................ 200202992

(51) Int. Cl.
*A61K 31/415*    (2006.01)
*C07D 233/00*    (2006.01)

(52) U.S. Cl. ........................ 514/399; 514/357; 546/329; 548/335.1; 548/341.1

(58) Field of Classification Search ................. 546/329; 548/335.1, 341.1; 514/399, 357
See application file for complete search history.

(56) References Cited

U.S. PATENT DOCUMENTS 5,162,340 A * 11/1992 Chakravarty et al. ........ 514/309

FOREIGN PATENT DOCUMENTS

| EP | 1122243 A1 | 8/2001 |
| WO | 9500501 A2 | 1/1995 |
| WO | 9636617 A1 | 11/1996 |
| WO | 9738986 A1 | 10/1997 |
| WO | 02083655 A1 | 10/2002 |

OTHER PUBLICATIONS

Tawada et al., 2003, CAS: 139:246034.*
Chakravarty et al., 1994, CAS: 120:45975.*
Almansa, Carmen, et al., "Synthesis and Structure-Activity Relationship of a New Series of COX-2 Selective Inhibitors: 1,5-Diarylimidazoles," Journal of Medicinal Chemistry, 46(16): 3463-3475 (Jul. 31, 2003).

* cited by examiner

*Primary Examiner*—Rei-tsang Shiao
(74) *Attorney, Agent, or Firm*—Rothwell Figg Ernst & Manbeck

(57) ABSTRACT

New phosphoramide derivatives of formula (I) and the salts and solvates thereof, wherein the meanings of the various substituents are as disclosed in the description. Said compounds are useful as antiinflammatory and analgesic agents.

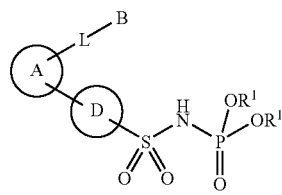

18 Claims, No Drawings

PHOSPHORAMIDE DERIVATIVES

This application is a 371 filing of PCT/EP2003/014818, filed Dec. 23, 2003, which claims priority from Spanish Application P 200202992, filed Dec. 24, 2002.

FIELD OF THE INVENTION

The present invention relates to a new series of phosphoramide derivatives, as well as to a process for their preparation, to the pharmaceutical compositions which comprise these compounds and to their use in medicine.

BACKGROUND OF THE INVENTION

In recent years, new antiinflammatory drugs, the so called coxibs or cyclooxygenase-2 (COX-2) inhibitors, which intend to avoid the commonly described gastric effects of non-steroidal antiinflammatory drugs (NSAIDs), have reached the market. Both kinds of drugs act by inhibiting cyclooxygenase, which is an enzyme that takes part in the arachidonic acid cascade by catalyzing the formation of substances such as prostaglandins ($PGE_2$, $PGD_2$, $PGF_2$), prostacyclin ($PGI_2$) and thromboxane $A_2$ ($TXA_2$), substances that, due to their vasoactive and inflammatory properties, are involved in numerous inflammatory processes, both acute and chronic.

The great difference between both kinds of drugs lies on the cyclooxygenase isoform upon which they act. In the early 90's, two cyclooxygenase isoforms, COX-1 and COX-2, were described. COX-1 is the constitutive form, present in many tissues, but preferentially in the stomach, kidney and platelets. Its inhibition is responsible for the gastric, renal and antiplatelet effects of NSAIDs, given that it leads to a reduction in the levels of prostaglandins, which at gastric level play a key role in the protection of the mucosa. On the other hand, COX-2 is an inducible form which is expressed as a consequence of an inflammatory or mitogenic stimulus in a wide range of tissues such as macrophages, chondrocytes, fibroblasts and endothelial cells. Selective inhibition of this isoform, mechanism on which the coxibs are based, is expected to render drugs with improved gastric tolerance.

Furthermore, COX-2 inhibition has proved to be an effective mechanism for the treatment of pain, especially for the treatment of severe and moderate pain resulting for example from traumatisms, acute diseases or surgery.

In the treatment of severe and moderate pain, especially in hospitals, the use of parenteral formulations is preferred in order to achieve a more rapid onset of action. Despite the fact that an inappropriate management of post-operative pain can lead to serious complications, long hospital stays, slower recoveries and an increase in the use of medications, its treatment is not solved at present in a satisfactory way. Thus, the use of the drugs currently available for this indication is limited due to the side effects with which they are associated: conventional NSAIDs are related to the above mentioned gastric and antiplatelet effects, while opioids, which are still more effective in the treatment of pain, are associated with sedating effects, constipation and respiratory depression. Moreover, most of the coxibs that are nowadays on the market or under development show water solubility values that do not contribute in any way to the development of injectable formulations. Thus, the present availability of injectable formulations for the treatment of pain is limited. Therefore, there remain a great need to find new compounds with antiinflammatory and analgesic activity which can be administered by parenteral route.

DESCRIPTION OF THE INVENTION

An aspect of the present invention relates to the new compounds of general formula I:

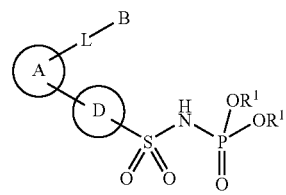

wherein:

each $R^1$ independently represents hydrogen, $C_{1-6}$ alkyl, $C_{1-6}$ haloalkyl, phenyl, heteroaryl or phenyl$C_{1-3}$ alkyl, where all phenyl and heteroaryl rings can be optionally substituted with one or more halogen, $C_{1-4}$ alkyl or $C_{1-4}$ alkoxy groups, or both substituents $R^1$ may be taken together to form a saturated or partially unsaturated 5- or 6-membered ring, which can be optionally fused to a benzene ring;

A represents an unsaturated or partially unsaturated 5- or 6-membered ring which can optionally contain from 1 to 3 heteroatoms selected from N, O and S, where the substituents L and D are placed on adjacent atoms of ring A, and where additionally A can be optionally substituted with one or more substituents $R^2$;

L represents a single bond, —O—, —S— or —$NR^3$—;

B represents $C_{1-6}$ alkyl or a ring selected from phenyl, heteroaryl and $C_{3-7}$ cycloalkyl, where all said rings can be optionally substituted with one or more substituents $R^4$;

D represents phenyl or pyridine, which can be both optionally substituted with one or more halogens;

the groups A and —$SO_2NHP(O)(OR^1)_2$ are placed on ring D in para position with respect to one another;

each $R^2$ independently represents halogen, cyano, nitro, carboxy, $C_{1-4}$ alkyl, $C_{2-4}$ alkenyl, $C_{2-4}$ alkynyl, $C_{1-4}$ haloalkyl, hydroxy, $C_{1-4}$ hydroxyalkyl, $C_{1-4}$ alkoxy, $C_{1-4}$ haloalkoxy, $C_{1-4}$ alkylthio, amino, $C_{1-4}$ alkylamino, $C_{1-4}$ dialkylamino, formyl, $C_{1-4}$ alkylcarbonyl, $C_{1-4}$ alkoxycarbonyl, $C_{1-4}$ haloalkoxycarbonyl, $C_{1-4}$ alkoxy$C_{1-3}$ alkyl, $C_{1-4}$ alkylcarbonyloxy$C_{1-3}$ alkyl, $C_{3-7}$ cycloalkyl$C_{1-4}$ alkoxy$C_{1-3}$ alkyl or $C_{3-7}$ cycloalkoxy$C_{1-3}$ alkyl, or two substituents $R^2$ on the same carbon atom can be taken together to form an oxo group;

$R^3$ represents hydrogen or $C_{1-4}$ alkyl;

each $R^4$ independently represents halogen, cyano, nitro, carboxy, $C_{1-4}$ alkyl $C_{1-4}$ haloalkyl, hydroxy, $C_{1-4}$ hydroxyalkyl, $C_{1-4}$ alkoxy, $C_{1-4}$ haloalkoxy, $C_{1-4}$ alkylthio, amino, $C_{1-4}$ alkylamino, $C_{1-4}$ dialkylamino, formyl, $C_{1-4}$ alkylcarbonyl, $C_{1-4}$ alkoxycarbonyl or $C_{1-4}$ haloalkoxycarbonyl, or two substituents $R^4$ on the same carbon atom can be taken together to form an oxo group, and additionally one of the substituents $R^4$ can represent a saturated, unsaturated or partially unsaturated 5- or 6-membered ring which can optionally contain from 1 to 3 heteroatoms selected from N, O and S and which can be optionally substituted with one or more substituents $R^5$;

each $R^5$ independently represents halogen, hydroxy, nitro, cyano, amino, $C_{1-4}$ alkyl, $C_{1-4}$ haloalkyl, $C_{1-4}$ alkoxy or $C_{1-4}$ alkylcarbonyl, or two substituents $R^5$ on the same carbon atom can be taken together to form an oxo group; and heteroaryl in the above definitions represents pyridine, pyrazine, pyrimidine or pyridazine.

The compounds of formula I are COX-2 inhibitors with good antiinflammatory and analgesic activity and moreover they are suitable for parenteral administration.

The present invention also relates to the salts of the compounds of formula I, as well as to their solvates.

Some compounds of formula I can have chiral centres, which can give rise to various stereoisomers. The present invention relates to each one of the individual stereoisomers as well as to their mixtures. Moreover, some of the compounds of the present invention can show cis/trans isomery. The present invention relates to each one of the geometric isomers as well as to their mixtures.

Another aspect of the present invention relates to the pharmaceutical compositions which comprise an effective amount of a compound of formula I or a pharmaceutically acceptable salt or solvate thereof and one or more pharmaceutically acceptable excipients.

Another aspect of the present invention relates to the use of a compound of formula I or a pharmaceutically acceptable salt or solvate thereof for the manufacture of a medicament for the treatment or prevention of diseases mediated by cyclooxygenase, especially cyclooxygenase-2. Preferably, the diseases mediated by cyclooxygenase-2 are selected from inflammation, pain, fever, pathologies associated with prostanoid-induced smooth muscle contraction, preneoplasic disorders, cancer, cerebral infarction, epilepsy, type I diabetes, neurodegenerative diseases and vascular diseases with an inflammatory component. More preferably, the compounds of the present invention are useful for the treatment or prevention of a disorder selected from the group consisting of: pain resulting from surgery or dental surgery; low back and neck pain; headache; toothache; pain associated with cancer; neuralgia; arthritis, including rheumatoid arthritis and juvenile arthritis; degenerative joint diseases, including osteoarthritis; gout; ankylosing spondylitis; tendinitis; pain and/or inflammation associated with traumatisms such as sprains, strains and other similar injuries, such as those produced during sport performance; synovitis; myositis; dysmenorrhea; inflammatory bowel disease; ocular inflammatory diseases, including conjunctivitis and endophthalmitis; corneal transplants; skin inflammatory diseases, including psoriasis, burns, eczema and dermatitis; systemic inflammatory processes, including sepsis and pancreatitis; bursitis; lupus erythematosus; common cold; rheumatic fever; symptoms associated with influenza or other viral infections; preterm labour; asthma; bronchitis; familial adenomatous polyposis; cancer, including liver, bladder, pancreas, ovary, prostate, cervix, lung, breast, skin cancer and gastrointestinal cancers such as colon cancer; cerebral infarction; epilepsy; type I diabetes; dementia, including Alzheimer's disease; Parkinson's disease; amyotrophic lateral sclerosis; and atherosclerosis.

Another aspect of the present invention relates to a compound of formula I or a pharmaceutically acceptable salt or solvate thereof for the treatment or prevention of diseases mediated by cyclooxygenase, especially cyclooxygenase-2. Preferably, the diseases mediated by cyclooxygenase-2 are selected from inflammation, pain, fever, pathologies associated with prostanoid-induced smooth muscle contraction, preneoplasic disorders, cancer, cerebral infarction, epilepsy, type I diabetes, neurodegenerative diseases and vascular diseases with an inflammatory component. More preferably, the compounds of the present invention are useful for the treatment or prevention of a disorder selected from the group consisting of: pain resulting from surgery or dental surgery; low back and neck pain; headache; toothache; pain associated with cancer; neuralgia; arthritis, including rheumatoid arthritis and juvenile arthritis; degenerative joint diseases, including osteoarthritis; gout; ankylosing spondylitis; tendinitis; pain and/or inflammation associated with traumatisms such as sprains, strains and other similar injuries, such as those produced during sport performance; synovitis; myositis; dysmenorrhea; inflammatory bowel disease; ocular inflammatory diseases, including conjunctivitis and endophthalmitis; corneal transplants; skin inflammatory diseases, including psoriasis, burns, eczema and dermatitis; systemic inflammatory processes, including sepsis and pancreatitis; bursitis; lupus erythematosus; common cold; rheumatic fever; symptoms associated with influenza or other viral infections; preterm labour; asthma; bronchitis; familial adenomatous polyposis; cancer, including liver, bladder, pancreas, ovary, prostate, cervix, lung, breast, skin cancer and gastrointestinal cancers such as colon cancer; cerebral infarction; epilepsy; type I diabetes; dementia, including Alzheimer's disease; Parkinson's disease; amyotrophic lateral sclerosis; and atherosclerosis.

Another aspect of the present invention relates to the use of a compound of formula I or a pharmaceutically acceptable salt or solvate thereof for the treatment or prevention of diseases mediated by cyclooxygenase, especially cyclooxygenase-2. Preferably, the diseases mediated by cyclooxygenase-2 are selected from inflammation, pain, fever, pathologies associated with prostanoid-induced smooth muscle contraction, preneoplasic disorders, cancer, cerebral infarction, epilepsy, type I diabetes, neurodegenerative diseases and vascular diseases with an inflammatory component. More preferably, the compounds of the present invention are useful for the treatment or prevention of a disorder selected from the group consisting of pain resulting from surgery or dental surgery; low back and neck pain; headache; toothache; pain associated with cancer; neuralgia; arthritis, including rheumatoid arthritis and juvenile arthritis; degenerative joint diseases, including osteoarthritis; gout; ankylosing spondylitis; tendinitis; pain and/or inflammation associated with traumatisms such as sprains, strains and other similar injuries, such as those produced during sport performance; synovitis; myositis; dysmenorrhea; inflammatory bowel disease; ocular inflammatory diseases, including conjunctivitis and endophthalmitis; corneal transplants; skin inflammatory diseases, including psoriasis, burns, eczema and dermatitis; systemic inflammatory processes, including sepsis and pancreatitis; bursitis; lupus erythematosus; common cold; rheumatic fever; symptoms associated with influenza or other viral infections; preterm labour; asthma; bronchitis; familial adenomatous polyposis; cancer, including liver, bladder, pancreas, ovary, prostate, cervix, lung, breast, skin cancer and gastrointestinal cancers such as colon cancer; cerebral infarction; epilepsy; type I diabetes; dementia, including Alzheimer's disease; Parkinson's disease; amyotrophic lateral sclerosis; and atherosclerosis.

Another aspect of the present invention relates to a method of treating or preventing diseases mediated by cyclooxygenase, especially cyclooxygenase-2, in a subject in need thereof, especially a human being, which comprises administering to said subject a therapeutically effective amount of a compound of formula I or a pharmaceutically acceptable salt or solvate thereof. Preferably, the diseases mediated by cyclooxygenase-2 are selected from inflammation, pain, fever, pathologies associated with prostanoid-induced smooth muscle contraction, preneoplasic disorders, cancer, cerebral infarction, epilepsy, type I diabetes, neurodegenerative diseases and vascular diseases with an inflammatory component. More preferably, the compounds of the present invention are useful for the treatment or prevention of a disorder selected from the group consisting of: pain resulting from surgery or dental surgery; low back and neck pain; headache; toothache, pain associated with cancer; neuralgia; arthritis, including rheumatoid arthritis and juvenile arthritis; degenerative joint diseases, including osteoarthritis; gout; ankylosing spondylitis; tendinitis; pain and/or inflammation associated with traumatisms such as sprains, strains and other similar injuries, such as those produced during sport performance; synovitis; myositis; dysmenorrhea; inflammatory bowel disease; ocular inflammatory diseases, including conjunctivitis and endophthalmitis; corneal transplants; skin inflammatory diseases, including psoriasis, burns, eczema and dermatitis; systemic inflammatory processes, including sepsis and pancreatitis; bursitis; lupus erythematosus; common cold; rheumatic fever; symptoms associated with influenza or other viral infections; preterm labour; asthma; bronchitis; familial adenomatous polyposis; cancer, including liver, bladder, pancreas, ovary, prostate, cervix, lung, breast, skin cancer and gastrointestinal cancers such as colon cancer; cerebral infarction; epilepsy; type I diabetes; dementia, including Alzheimer's disease; Parkinson's disease; amyotrophic lateral sclerosis; and atherosclerosis.

Another aspect of the present invention relates to a process for preparing a compound of formula I, which comprises:

(a) when in a compound of formula I each $R^1$ is different from hydrogen, reacting a sulfonamide of formula II

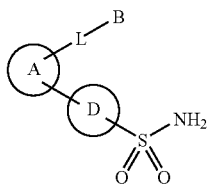

wherein A, L, B and D have the meaning described above, with a compound of formula III $$XP(O)(OR^{1a})_2 \quad \text{III}$$

wherein X represents H or Cl and wherein each $R^{1a}$ independently represents any of the meanings described above for $R^1$ except for hydrogen, in the presence of a base, or alternatively, reacting a sulfonamide of formula II in which the group —$SO_2NH_2$ is in anionic form with a compound of formula III;

(b) when in a compound of formula I each $R^1$ represents hydrogen, hydrolysing a compound of formula Ia'

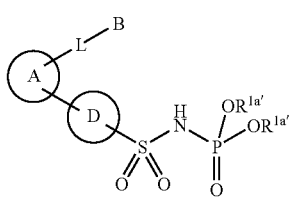

wherein A, L, B and D have the meaning described above and wherein $R^{1a'}$ represents any of the meanings described above for $R^1$ except for hydrogen and benzyl, or alternatively, hydrogenating a compound of formula Ia"

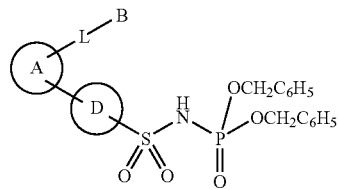

wherein A, L, B and D have the meaning described above;

(c) when in a compound of formula I one of the substituents $R^1$ represents hydrogen and the other is different from hydrogen, monodealkylating a compound of formula Ia'''

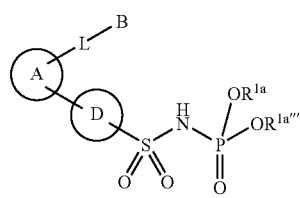

wherein A, L, B, D and $R^{1a}$ have the meaning described above and wherein $R^{1a'''}$ represents $C_{1-6}$ alkyl, $C_{1-6}$ haloalkyl or phenyl$C_{1-3}$ alkyl, where the phenyl group can be optionally substituted with one or more halogen, $C_{1-4}$ alkyl or $C_{1-4}$ alkoxy groups;

(d) transforming, in one or a plurality of steps, a compound of formula I into another compound of formula I; and (e) if desired, after the above steps, reacting a compound of formula I with a base or an acid to give the corresponding addition salt.

In the above definitions, the term $C_{1-3}$, $C_{1-4}$ or $C_{1-6}$ alkyl, as a group or part of a group, means a linear or branched alkyl group that contains from 1 to 3, from 1 to 4 or from 1 to 6 carbon atoms, respectively. Examples include among others the groups methyl, ethyl, propyl, isopropyl, butyl, isobutyl, sec-butyl, tert-butyl, pentyl, isopentyl, neopentyl and hexyl.

A $C_{2-4}$ alkenyl group means a linear or branched alkyl chain that contains from 2 to 4 carbon atoms, and that in addition contains one or more double bonds. Examples include among others the groups ethenyl, 1-propenyl, 2-propenyl, isopropenyl, 1-butenyl, 2-butenyl, 3-butenyl and 1,3-butadienyl.

A $C_{2-4}$ alkynyl group means a linear or branched alkyl chain that contains from 2 to 4 carbon atoms, and that in addition contains one or more triple bonds. Examples include among others the groups ethynyl, i-propynyl, 2-propynyl, 1-butynyl, 2-butynyl and 3-butynyl.

A halogen radical or its abbreviation halo means fluoro, chloro, bromo or iodo.

A $C_{1-4}$ or $C_{1-6}$ haloalkyl group means a group resulting from the substitution of one or more hydrogen atoms of a $C_{1-4}$ or $C_{1-6}$ alkyl group, respectively, with one or more halogen atoms (that is fluoro, chloro, bromo or iodo), which can be the same or different. Examples include among others the groups trifluoromethyl, fluoromethyl, 1-chloroethyl, 2-chloroethyl, 1-fluoroethyl, 2-fluoroethyl, 2-bromoethyl, 2-iodoethyl, 2,2, 2-trifluoroethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl, nonafluorobutyl, 5-fluoropentyl and 6-fluorohexyl.

A $C_{1-4}$ hydroxyalkyl group means a group resulting from the substitution of one or more hydrogen atoms of a $C_{1-4}$ alkyl group with one or more hydroxy groups. Examples include among others hydroxymethyl, 1-hydroxyethyl, 2-hydroxyethyl, 3-hydroxypropyl and 4-hydroxybutyl.

A phenyl$C_{1-3}$ alkyl group means a group resulting from the substitution of a hydrogen atom of a $C_{1-3}$ alkyl group with a phenyl group (wherein said phenyl ring can be optionally substituted as described above in the definition of $R^1$). Examples include among others the groups benzyl, 1-phenylethyl, 2-phenylethyl, 1-phenylpropyl, 2-phenylpropyl and 3-phenylpropyl, and the corresponding groups where the phenyl ring is substituted.

A $C_{1-4}$ alkoxy group means a group resulting from attaching a $C_{1-4}$ alkyl group to an ether-type oxygen atom. Examples thereof are the groups methoxy, ethoxy, propoxy, isopropoxy, butoxy, isobutoxy, sec-butoxy and tert-butoxy.

A $C_{1-4}$ alkoxy$C_{1-3}$ alkyl group means a group resulting from the substitution of a hydrogen atom of a $C_{1-3}$ alkyl group with a $C_{1-4}$ alkoxy group as defined above. Examples include among others methoxymethyl, ethoxymethyl, propoxymethyl, isopropoxymethyl, 2-(methoxy)ethyl, 2-(ethoxy)ethyl and 3-(methoxy)propyl.

A $C_{1-4}$ haloalkoxy group means a group resulting from the substitution of one or more hydrogen atoms of a $C_{1-4}$ alkoxy group with one or more halogen atoms, which can be the same or different. Examples include among others trifluoromethoxy, fluoromethoxy, 1-chloroethoxy, 2-chloroethoxy, 1-fluoroethoxy, 2-fluoroethoxy, 2-bromoethoxy, 2-iodoethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy and nonafluorobutoxy.

A $C_{1-4}$ alkylamino or $C_{1-4}$ dialkylamino group represents a group resulting from the substitution of one or two hydrogen atoms respectively of an amino group with one or two $C_{1-4}$ alkyl groups, which can be the same or different. Examples include among others methylamino, dimethylamino, ethylamino, diethylamino, ethylmethylamino, propylamino, dipropylamino, isopropylamino, diisopropylamino and butylamino.

A $C_{1-4}$ alkylcarbonyl group means a group resulting from attaching a $C_{1-4}$ alkyl group to a carbonyl group. Examples thereof include among others the groups methylcarbonyl, ethylcarbonyl, propylcarbonyl, isopropylcarbonyl, butylcarbonyl, isobutylcarbonyl, sec-butylcarbonyl and tert-butylcarbonyl.

A $C_{1-4}$alkoxycarbonyl group means a group resulting from attaching a $C_{1-4}$ alkoxy group to a carbonyl group. Examples thereof include among others the groups methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl.

A $C_{1-4}$ haloalkoxycarbonyl group means a group resulting from attaching a $C_{1-4}$ haloalkoxy group to a carbonyl group. Examples include among others trifluoromethoxycarbonyl, fluoromethoxycarbonyl, 1-chloroethoxycarbonyl, 2-chloroethoxycarbonyl, 1-fluoroethoxycarbonyl, 2-fluoroethoxycarbonyl, 2-bromoethoxycarbonyl, 2-iodoethoxycarbonyl, 2,2,2-trifluoroethoxycarbonyl, pentafluoroethoxycarbonyl, 3-fluoropropoxycarbonyl, 3-chloropropoxycarbonyl, 2,2,3,3-tetrafluoropropoxycarbonyl, 2,2,3,3,3-pentafluoropropoxycarbonyl, heptafluoropropoxycarbonyl, 4-fluorobutoxycarbonyl and nonafluorobutoxycarbonyl.

A $C_{1-4}$ alkylcarbonyloxy group (that is, a group $C_{1-4}$ alkylCOO—) means a group resulting from attaching a $C_{1-4}$ alkylcarbonyl group as defined above to an oxygen atom. Examples thereof include among others the groups methylcarbonyloxy, ethylcarbonyloxy, propylcarbonyloxy, isopropylcarbonyloxy, butylcarbonyloxy, isobutylcarbonyloxy, sec-butylcarbonyloxy and tert-butylcarbonyloxy.

A $C_{1-4}$ alkylcarbonyloxy$C_{1-3}$ alkyl group means a group resulting from the substitution of a hydrogen atom of a $C_{1-3}$ alkyl group with a $C_{1-4}$ alkylcarbonyloxy group as defined above. Examples include among others the groups methylcarbonyloxymethyl, ethylcarbonyloxymethyl, propylcarbonyloxymethyl, isopropylcarbonyloxymethyl, butylcarbonyloxymethyl, isobutylcarbonyloxymethyl, sec-butylcarbonyloxymethyl, tert-butylcarbonyloxymethyl, 2-(methylcarbonyloxy)ethyl and 3-(methylcarbonyloxy)propyl.

A $C_{1-4}$ alkylthio group means a group resulting from attaching a $C_{1-4}$ alkyl group to a thioether-type sulfur atom. Examples thereof include among others the groups methylthio, ethylthio, propylthio, isopropylthio, butylthio, isobutylthio, sec-butylthio and tert-butylthio.

The term $C_{3-7}$ cycloalkyl, as a group or part of a group, represents cyclopropyl, cyclobutyl, cyclopentyl, cyclohexyl or cycloheptyl.

A $C_{3-7}$ cycloalkoxy group represents a group resulting from attaching a $C_{3-7}$ cycloalkyl group as defined above to an ether-type oxygen atom. Examples thereof include the groups cyclopropoxy, cyclobutoxy, cyclopentyloxy, cyclohexyloxy and cycloheptyloxy.

A $C_{3-7}$ cycloalkoxy$C_{1-3}$ alkyl group represents a group resulting from the substitution of a hydrogen atom of a $C_{1-3}$ alkyl group with a $C_{3-7}$ cycloalkoxy group as defined above. Examples thereof include among others the groups cyclopropoxymethyl, cyclobutoxymethyl, cyclopentyloxymethyl, cyclohexyloxymethyl, cycloheptyloxymethyl, 2-(cyclopropoxy)ethyl and 3-(cyclopropoxy)propyl.

A $C_{3-7}$ cycloalkyl$C_{1-4}$ alkoxy$C_{1-3}$ alkyl group represents a group resulting from the substitution of a hydrogen atom of a $C_{1-4}$ alkoxy group that belongs to a $C_{1-4}$ alkoxy$C_{1-3}$ alkyl group with a $C_{3-7}$ cycloalkyl group as defined above. Examples include among others the groups cyclopropylmethoxymethyl and cyclobutylmethoxymethyl.

The term unsaturated ring refers to a ring that possesses in its structure the highest possible number of double bonds.

The term partially unsaturated ring refers to a ring that possesses at least one double bond in its structure but that does not possess the highest possible number of double bonds.

The term oxo means a carbonyl group.

In the compounds of formula I, $R^1$ independently represents hydrogen, $C_{1-6}$ alkyl, $C_{1-6}$ haloalkyl, phenyl, heteroaryl or phenyl$C_{1-3}$ alkyl, where the phenyl (either in the phenyl group or in the phenyl$C_{1-3}$ alkyl group) and heteroaryl rings can be optionally substituted with one or more halogen, $C_{1-4}$ alkyl or $C_{1-4}$ alkoxy groups. Additionally, both substituents $R^1$ can be taken together to form with the P atom and the two O atoms to which the $R^1$ groups are bound a saturated or partially unsaturated 5- or 6-membered ring. Said ring cannot contain in its structure more heteroatoms than the P atom and the two O atoms bound to $R^1$ depicted in formula I, and can be optionally fused to a benzene ring through any available carbon-carbon bond in its structure. Examples of said ring include, among others, [1,3,2]dioxaphospholane, [1,3,2]dioxaphosphinane and benzo[1,3,2]dioxaphosphole. Among all the meanings described for $R^1$, $R^1$ preferably represents hydrogen, $C_{1-6}$ alkyl or phenyl (where the phenyl group can be optionally substituted with one or more halogen, $C_{1-4}$ alkyl or $C_{1-4}$ alkoxy groups).

In the compounds of the present invention, ring A represents an unsaturated or partially unsaturated 5- or 6-membered ring which can be carbocyclic or heterocyclic, in which case it can contain from 1 to 3 heteroatoms selected from N, O and S. The L and D substituents are placed on adjacent atoms of ring A. Ring A can be substituted with L and D alone, or additionally can have one or more, preferably from one to four, more preferably from one to two, substituents $R^2$, which can be the same or different and which can be placed on any available position of ring A, that is, either on a carbon atom or on an available nitrogen atom in the case of heterocyclic rings. Preferred examples of ring A include imidazole, pyrazole, isoxazole, oxazole, thiazole, 2,5-dihydrofuran, thiophene, pyridine, 4H-pyran, 2H-pyran, cyclopentene, 2,3-dihydrooxazole and 4,5-dihydropyrazole, of which imidazole, pyrazole, isoxazole, oxazole, 2,5-dihydrofuran and 4H-pyran are more preferred, imidazole, pyrazole, isoxazole and oxazole are still more preferred and imidazole is especially preferred.

As defined above, each $R^2$ independently represents halogen, cyano, nitro, carboxy, $C_{1-4}$ alkyl, $C_{2-4}$ alkenyl, $C_{2-4}$ alkynyl, $C_{1-4}$ haloalkyl, hydroxy, $C_{1-4}$ hydroxyalkyl, $C_{1-4}$ alkoxy, $C_{1-4}$ haloalkoxy, $C_{1-4}$ alkylthio, amino, $C_{1-4}$ alkylamino, $C_{1-4}$ dialkylamino, formyl, $C_{1-4}$ alkylcarbonyl, $C_{1-4}$ alkoxycarbonyl, $C_{1-4}$ haloalkoxycarbonyl, $C_{1-4}$ alkoxy$C_{1-3}$ alkyl, $C_{1-4}$ alkylcarbonyloxy$C_{1-3}$ alkyl, $C_{3-7}$ cycloalkyl$C_{1-4}$ alkoxy$C_{1-3}$ alkyl or $C_{3-7}$ cycloalkoxy$C_{1-3}$ alkyl. Moreover, two substituents $R^2$ on the same carbon atom may be taken together to form an oxo group.

Although ring A can be optionally substituted with one or more substituents $R^2$ as defined above, examples of preferred substituents $R^2$ include halogen, $C_{1-4}$ alkyl, $C_{1-4}$ haloalkyl and oxo. As preferred examples of ring A substituted with one or more substituents $R^2$, the groups 4-chloroimidazole, 3-trifluoromethylpyrazole, 3-difluoromethylpyrazole, 5-methylisoxazole, 2-methyloxazole, 2-methylthiazole, 3H-2-oxazolone, 5H-2-furanone, 2-bromothiophene, 3-chloropyridine, 4H-4-pyranone, 2H-2-pyranone and 4H-3-methyl-4-pyranone can be mentioned, of which 4-chloroimidazole, 3-trifluoromethylpyrazole, 5-methylisoxazole and 2-methyloxazole are more preferred, and 4-chloroimidazole is especially preferred.

L can represent a single bond, —O—, —S— or —NR³—, but preferably represents a single bond or —O—, and more preferably represents a single bond.

In the compounds of the present invention, B can represent $C_{1-6}$ alkyl or a ring selected from phenyl, heteroaryl and $C_{3-7}$ cycloalkyl. When B represents phenyl, heteroaryl or $C_{3-7}$ cycloalkyl, these rings can be optionally substituted with one or more, preferably one to three, substituents $R^4$ as defined above, which can be the same or different and which can be placed on any available position of ring B. When L represents a single bond, B preferably represents a phenyl, heteroaryl or $C_{3-7}$ cycloalkyl group optionally substituted with one to three substituents $R^4$, more preferably B represents either phenyl optionally substituted with one to three groups $R^4$ or cyclohexyl, and still more preferably B represents phenyl optionally substituted with one to three groups $R^4$. When L represents —O—, B preferably represents either $C_{1-6}$ alkyl or phenyl optionally substituted with one to three substituents $R^4$, and more preferably B represents isopropyl or phenyl optionally substituted with one to three substituents $R^4$.

As defined above, $R^4$ can represent halogen, cyano, nitro, carboxy, $C_{1-4}$ alkyl, $C_{1-4}$ haloalkyl, hydroxy, $C_{1-4}$ hydroxyalkyl, $C_{1-4}$ alkoxy, $C_{1-4}$ haloalkoxy, $C_{1-4}$ alkylthio, amino, $C_{1-4}$ alkylamino, $C_{1-4}$ dialkylamino, formyl, $C_{1-4}$ alkylcarbonyl, $C_{1-4}$ alkoxycarbonyl or $C_{1-4}$ haloalkoxycarbonyl. Additionally, two substituents $R^4$ on the same carbon atom may be taken together to form an oxo substituent. Additionally, one of the substituents $R^4$ can represent a saturated, unsaturated or partially unsaturated 5- or 6-membered ring, which can be carbocyclic or heterocyclic, in which case it can contain from 1 to 3 heteroatoms selected from N, O and S. When $R^4$ represents one of said rings, these can be optionally substituted with one or more, preferably one to three, substituents $R^5$ as defined above, which can be the same or different and which can be placed on any available position of the ring, either on a carbon atom or on a nitrogen atom in the case of heterocyclic rings. Examples of $R^4$ rings include among others benzene, pyridine, piperidine, pyrrolidine, pyrroline, oxazolidine, pyrrole and imidazole, among which pyrrolidine is a preferred group. Among all the possible meanings for $R^4$, the groups halogen, $C_{1-4}$ alkyl, $C_{1-4}$ alkoxy and $C_{1-4}$ haloalkyl are preferred.

In the compounds of the present invention D represents phenyl or pyridine, which can be optionally substituted with one or more, preferably one, halogen atoms, which can be the same or different and can be on any available position of ring D. The groups A and —SO₂NHP(O)(OR¹)₂ are always placed on ring D in para position with respect to one another. Fluoro is the halogen preferred as ring D substituent. Preferably, D represents phenyl optionally substituted with a fluoro atom or D is pyridine, more preferably D is phenyl optionally substituted with a fluoro atom and still more preferably D is phenyl.

Although the present invention includes all the compounds mentioned above, those compounds of formula I wherein A represents imidazole, pyrazole, isoxazole, oxazole, thiazole, 2,5-dihydrofuran, thiophene, pyridine, 4H-pyran, cyclopentene, 2,3-dihydrooxazole or 4,5-dihydropyrazole, which can be optionally substituted with one to four substituents $R^2$, as well as the salts and solvates thereof, are preferred.

Another preferred class of compounds of the present invention are those compounds of formula I wherein:

A represents imidazole, pyrazole, isoxazole, oxazole, thiazole, 2,5-dihydrofuran, thiophene, pyridine, 4H-pyran, cyclopentene, 2,3-dihydrooxazole or 4,5-dihydropyrazole, which can be optionally substituted with one to four substituents $R^2$; and D represents phenyl optionally substituted with a fluoro atom; and the salts and solvates thereof.

Another preferred class of compounds of the present invention are those compounds of formula I wherein:

A represents imidazole, pyrazole, isoxazole, oxazole, thiazole, 2,5-dihydrofuran, thiophene, pyridine, 4H-pyran, cyclopentene, 2,3-dihydrooxazole or 4,5-dihydropyrazole, which can be optionally substituted with one to four substituents $R^2$;

D represents phenyl optionally substituted with a fluoro atom;

L represents a single bond; and

B represents phenyl, heteroaryl or $C_{3-7}$ cycloalkyl, which can all be optionally substituted with one to three groups $R^4$;

and the salts and solvates thereof.

Another preferred class of compounds of the present invention are those compounds of formula I wherein:

A represents imidazole, pyrazole, isoxazole, oxazole, thiazole, 2,5-dihydrofuran, thiophene, pyridine, 4H-pyran, cyclopentene, 2,3-dihydrooxazole or 4,5-dihydropyrazole, which can be optionally substituted with one to four substituents $R^2$;

each $R^2$ independently represents halogen, $C_{1-4}$ alkyl or $C_{1-4}$ haloalkyl, or two substituents $R^2$ on the same carbon atom can be taken together to form an oxo group;

D represents phenyl optionally substituted with a fluoro atom;

L represents a single bond; and

B represents phenyl, heteroaryl or $C_{3-7}$ cycloalkyl, which can all be optionally substituted with one to three groups $R^4$;

and the salts and solvates thereof.

Another preferred class of compounds of the present invention are those compounds of formula I wherein:

A represents imidazole, pyrazole, isoxazole, oxazole, thiazole, 2,5-dihydrofuran, thiophene, pyridine, 4H-pyran, cyclopentene, 2,3-dihydrooxazole or 4,5-dihydropyrazole, which can be optionally substituted with one to four substituents $R^2$;

each $R^2$ independently represents halogen, $C_{1-4}$ alkyl or $C_{1-4}$ haloalkyl, or two substituents $R^2$ on the same carbon atom can be taken together to form an oxo group;

D represents phenyl optionally substituted with a fluoro atom;

L represents a single bond; and

B represents phenyl optionally substituted with one to three groups $R^4$, or B represents cyclohexyl;

and the salts and solvates thereof.

Another preferred class of compounds of the present invention are those compounds of formula I wherein:

A represents imidazole, pyrazole, isoxazole, oxazole, thiazole, 2,5-dihydrofuran, thiophene, pyridine, 4H-pyran, cyclopentene, 2,3-dihydrooxazole or 4,5-dihydropyrazole, which can be optionally substituted with one to four substituents $R^2$;

each $R^2$ independently represents halogen, $C_{1-4}$ alkyl or $C_{1-4}$ haloalkyl, or two substituents $R^2$ on the same carbon atom can be taken together to form an oxo group;

D represents phenyl optionally substituted with a fluoro atom;

L represents a single bond;

B represents phenyl optionally substituted with one to three groups $R^4$, or B represents cyclohexyl; and each $R^4$ independently represents halogen, $C_{1-4}$ alkyl, $C_{1-4}$ alkoxy or $C_{1-4}$ haloalkyl;

and the salts and solvates thereof.

Another preferred class of compounds of the present invention are those compounds of formula I wherein:

A represents imidazole, pyrazole, isoxazole, oxazole, thiazole, 2,5-dihydrofuran, thiophene, pyridine, 4H-pyran, cyclopentene, 2,3-dihydrooxazole or 4,5-dihydropyrazole, which can be optionally substituted with one to four substituents $R^2$;

D represents phenyl optionally substituted with a fluoro atom;

L represents —O—; and

B represents $C_{1-6}$ alkyl or phenyl optionally substituted with one to three substituents $R^4$;

and the salts and solvates thereof.

Another preferred class of compounds of the present invention are those compounds of formula I wherein:

A represents 4H-4-pyranone optionally substituted with one or two substituents $R^2$;

D represents phenyl;

L represents —O—;

B represents phenyl optionally substituted with one to three substituents $R^4$; and each $R^4$ independently represents halogen, $C_{1-4}$ alkyl, $C_{1-4}$ alkoxy or $C_{1-4}$ haloalkyl;

and the salts and solvates thereof.

Another preferred class of compounds of the present invention are those compounds of formula I wherein:

A represents 5H-2-furanone optionally substituted with one or two substituents $R^2$;

D represents phenyl;

L represents —O—; and

B represents isopropyl;

and the salts and solvates thereof.

A more preferred class of compounds of the present invention are those compounds of formula I wherein:

A represents imidazole, pyrazole, isoxazole or oxazole, which can be optionally substituted with one or two substituents $R^2$;

each $R^2$ independently represents halogen, $C_{1-4}$ alkyl or $C_{1-4}$ haloalkyl;

D represents phenyl optionally substituted with a fluoro atom;

L represents a single bond;

B represents phenyl optionally substituted with one to three groups $R^4$ or B represents cyclohexyl; and each $R^4$ independently represents halogen, $C_{1-4}$ alkyl, $C_{1-4}$ alkoxy or $C_{1-4}$ haloalkyl;

and the salts and solvates thereof.

A still more preferred class of compounds of the present invention are those compounds of formula Id:

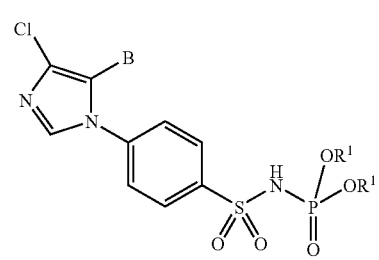

Id wherein:

B represents phenyl optionally substituted with one to three groups $R^4$; and each $R^4$ independently represents halogen, $C_{1-4}$ alkyl, $C_{1-4}$ alkoxy or $C_{1-4}$ haloalkyl;

and the salts and solvates thereof.

An even more preferred class of compounds of the present invention are those compounds of formula Id wherein:

B represents phenyl optionally substituted with one to three groups $R^4$;

each $R^4$ independently represents halogen, $C_{1-4}$ alkyl, $C_{1-4}$ alkoxy or $C_{1-4}$ haloalkyl; and each $R^1$ independently represents hydrogen, $C_{1-6}$ alkyl or phenyl optionally substituted with one or more halogen, $C_{1-4}$ alkyl or $C_{1-4}$ alkoxy groups;

and the salts and solvates thereof.

An especially preferred class of compounds of the present invention are those compounds of formula Id wherein:

B represents 3-fluoro-4-methoxyphenyl; and each $R^1$ independently represents hydrogen, $C_{1-6}$ alkyl or phenyl optionally substituted with one or more halogen, $C_{1-4}$ alkyl or $C_{1-4}$ alkoxy groups;

and the salts and solvates thereof.

In a particularly preferred embodiment of the invention, the compound of formula I is N-[4-[4-chloro-5-(3-fluoro-4-methoxyphenyl)imidazol-1-yl]phenylsulfonyl]phosphoramidic acid and the salts and solvates thereof.

In the above definitions of preferred embodiments of the invention, when the meaning of a certain substituent is not specified it means that said substituent has the same meaning as in formula I.

The compounds of the present invention contain one or more acid protons and in some cases can contain one or more basic nitrogens and, consequently, they can form salts with organic and inorganic bases and acids, which are also included in the present invention. There is no limitation on the nature of said salts, provided that, when used for therapeutic purposes, they are pharmaceutically acceptable. Examples of said salts include: salts with inorganic cations such as sodium, potassium, calcium, magnesium, lithium, aluminum, zinc, etc; salts formed with pharmaceutically acceptable amines such as ammonia, alkylamines, hydroxyalkylamines, lysine, arginine, N-methylglucamine, procaine and the like; salts with inorganic acids such as hydrochloric acid, hydrobromic acid, hydriodic acid, nitric acid, perchloric acid, sulfuric acid or phosphoric acid; and salts with organic acids, such as methanesulfonic acid, trifluoromethanesulfonic acid, ethanesulfonic acid, benzenesulfonic acid, p-toluenesulfonic acid, fumaric acid, oxalic acid, acetic acid or maleic acid, among others. The salts can be prepared by conventional methods, for example from a compound of formula I by treatment with a sufficient amount of the desired base or acid to give the salt in a conventional manner, or from a salt previously obtained from a compound of formula I, by ion exchange, using an ion exchange resin. The compounds of formula I and their salts differ in certain physical properties, such as solubility, but they are equivalent for the purposes of the invention.

Some compounds of the present invention can exist in solvated form, including hydrated forms. In general, the solvated forms, with pharmaceutically acceptable solvents such as water, ethanol and the like, are equivalent to the unsolvated form for the purposes of the invention.

Some compounds of the present invention may exist as various diastereoisomers and/or various optical isomers. Diastereoisomers can be separated by conventional techniques such as chromatography or fractional crystallization. The optical isomers can be resolved using conventional techniques of optical resolution, to give the optically pure isomers. This resolution can be performed upon any chiral synthetic intermediate or upon the products of general formula I. The optically pure isomers can also be individually obtained using enantioespecific synthesis. The present invention covers both the individual isomers and the mixtures (for example racemic mixtures), whether obtained by synthesis or by physically mixing them up.

Furthermore, some of the compounds of the present invention can exhibit cis/trans isomery. The present invention includes each one of the geometric isomers as well as the mixtures thereof.

The present invention also provides a process for the preparation of the compounds of formula I. As it will be obvious to a person skilled in the art, the precise method used for the preparation of a given compound can vary depending on its chemical structure. Furthermore, in some of the processes that are explained below it may be necessary or advisable to protect the reactive or labile groups using conventional protecting groups. Both the nature of said protecting groups and the processes for their introduction and removal are well known and belong to the state of the art (see for example Greene T. W. and Wuts P. G. M, "Protective Groups in Organic Synthesis", John Wiley & Sons, $3^{rd}$ edition, 1999). Whenever a protecting group is present, a later deprotection step will be necessary, which is performed under standard conditions, such as those described in the reference above mentioned.

The compounds of the present invention are generally obtained from a sulfonamide of formula II,

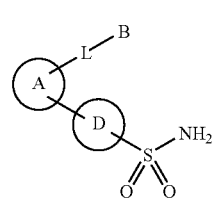

II wherein A, L, B and D have the meaning described above. Said sulfonamide is transformed into the desired compound of formula I by chemical processes that generally are carried out in one, two or three steps as needed.

Thus, the compounds of formula I where each $R^1$ is different from hydrogen (that is, compounds of formula Ia)

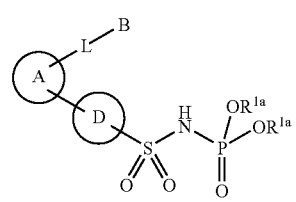

Ia wherein A, L, B and D have the meaning described above and wherein each $R^{1a}$ independently represents any of the meanings described above for $R^1$ except for hydrogen, can be obtained by condensation of a sulfonamide of formula II with a compound of formula III

$XP(O)(OR^{1a})_2$    III wherein X represents H or chloro and $R^{1a}$ has the meaning described above, in the presence of a base such as NaOH or KOH and in a suitable solvent such as a polar solvent, for example tetrahydrofuran, dimethoxyethane or acetonitrile, when X represents Cl, or in a halogenated solvent such as carbon tetrachloride or chloroform when X represents hydrogen. The reaction is carried out between 0° C. and reflux, preferably between 0° C. and room temperature when X represents hydrogen.

Alternatively, this transformation can be carried out in two steps, forming first the salt of the sulfonamide of formula II by treatment with one equivalent of a base such as NaOH or KOH, in a suitable solvent such as a polar hydroxylic solvent, for example ethanol or isopropanol, and reacting in a second step the salt obtained with a compound of formula III, in a inert polar solvent such as tetrahydrofuran, dimethoxyethane or acetonitrile when X represents Cl, or in a halogenated solvent such as carbon tetrachloride or chloroform when X represents hydrogen. The process is carried out between 0° C. and reflux.

The compounds of formula III are commercially available, such as dimethyl chlorophosphate, diethyl chlorophosphate, diphenyl chlorophosphate, diphenyl phosphate, 2-chloro[1,3,2]dioxaphospholane 2-oxide and 2-chlorobenzo[1,3,2]dioxaphosphole 2-oxide, or they can be obtained by methods widely described in the literature for this kind of compounds, for example by reaction of $POCl_3$ or $PCl_3$ with the desired alcohol or alcohols (when the two groups $R^1$ are different, in which case the reaction is carried out by adding the two alcohols in successive steps) in the presence of a base such as triethylamine or N-methylmorpholine in an aprotic solvent such as for example a halogenated solvent, benzene or toluene.

The compounds of formula I where each $R^1$ represents hydrogen (that is, compounds of formula Ib)

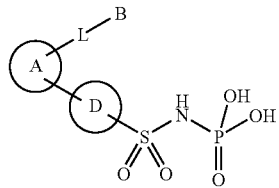

Ib wherein A, L, B and D have the meaning described above, can be obtained in general from a phosphodiester of formula Ia by removal of the group $R^{1a}$.

When $R^{1a}$ represents any of the meanings described above for $R^1$ except for hydrogen and benzyl (that is $R^{1a'}$), the compounds of formula Ib can be obtained by hydrolysis of a compound of formula Ia'

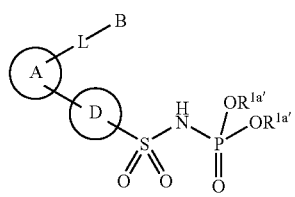

Ia' wherein A, L, B, D and $R^{1a'}$ have the meaning described above. In general the transformation is carried out by treating the phosphodiester first with a suitable reagent for the hydrolysis of phosphodiesters such as bromotrimethylsilane or iodotrimethylsilane in an inert solvent such as dichloromethane or acetonitrile and then with an acetone/water mixture. This reaction is carried out at a temperature comprised between 0° C. and reflux, preferably at a temperature comprised between 0° C. and room temperature.

In the case of benzyl phosphodiesters, that is, when $R^{1a}$ represents benzyl, the compounds of formula Ib can be obtained by hydrogenation of a benzyl phosphodiester of formula Ia",

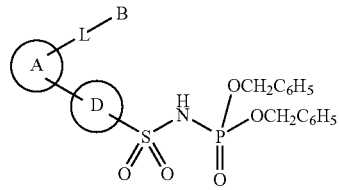

Ia"

wherein A, L, B and D have the meaning described above. This reaction is carried out in the presence of a catalyst such as Pd/C, in a suitable solvent such as an alcohol, for example methanol or ethanol, and at a temperature comprised between 0° C. and reflux, preferably at room temperature.

Moreover, compounds of formula I where one of the substituents $R^1$ represents hydrogen and the other is different from hydrogen (that is, compounds of formula Ic)

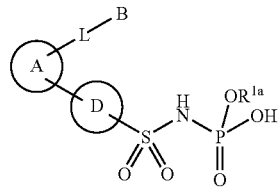

Ic wherein A, L, B, D and $R^{1a}$ have the meaning described above, can also be obtained by monodealkylation of a phosphodiester of formula Ia where at least one of the groups $R^{1a}$ represents an alkyl-type group (that is, a compound of formula Ia''')

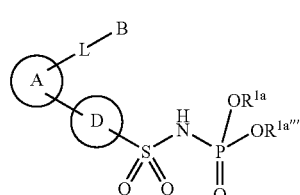

Ia''' wherein A, L, B, D and $R^{1a}$ have the meaning described above and $R^{1a'''}$ represents $C_{1-6}$ alkyl, $C_{1-6}$ haloalkyl or phenyl$C_{1-3}$ alkyl (where the phenyl ring can be optionally substituted with one or more halogen, $C_{1-4}$ alkyl or $C_{1-4}$ alkoxy groups). This reaction is carried out by treating said phosphodiester Ia''' with a suitable reagent for the monodealkylation of phosphodiesters, for example a iodine salt such as sodium iodide or potassium iodide, in a suitable solvent such as acetone and at a temperature comprised between room temperature and reflux, preferably at reflux. Given that the product resulting from the reaction is a sodium or potassium salt depending on the reagent used, the compound of formula Ic can then be obtained by treatment of the salt obtained with an acid, for example an inorganic acid such as for example hydrochloric acid, hydrobromic acid, hydriodic acid, nitric acid, perchloric acid, sulfuric acid or phosphoric acid, or with an organic acid such as for example methanesulfonic acid, trifluoromethanesulfonic acid, ethanesulfonic acid, benzenesulfonic acid, p-toluenesulfonic acid, fumaric acid, oxalic acid, acetic acid or maleic acid, among others.

Moreover, the compounds of formula I can also be obtained by interconversion from another compound of formula I. For example, a compound of formula Ib can be converted into a compound of formula Ia by esterification, or a compound of formula Ia can be interconverted into another compound of formula Ia by introduction of a substituent $R^2$ onto the corresponding compound Ia where ring A is unsubstituted, or by transformation of a substituent $R^2$ or $R^4$ into another group $R^2$ or $R^4$, respectively, in one or a plurality of steps, using standard reactions in heterocyclic chemistry, widely described in the literature.

The starting sulfonamides of formula II can be obtained according to methods widely described in the literature, such as for example those described in the following references: WO 00/23426 for the preparation, among others, of compounds where A is imidazole, WO 95/15316 for the preparation of compounds where A is pyrazole, WO 96/25405 for the preparation of compounds where A is isoxazole, WO 97/34882 for the preparation of compounds where A is 3H-2-oxazolone, EP 745596 for the preparation of compounds where A is oxazole, WO 95/11883 for the preparation of compounds where A is cyclopentene, WO 96/03392 for the preparation of compounds where A is thiazole, WO 00/18753 and WO 01/68633 for the preparation of compounds where A is 4H-4-pyranone, WO 03/006451 for the preparation of compounds where A is 2H-2-pyranone, WO 98/03484 for the preparation of compounds where A is pyridine, WO 95/00501 and WO 97/14691 for the preparation, among others, of compounds where A is 5H-2-furanone or thiophene, WO 99/62884 for the preparation of compounds where A is 4,5-dihydropyrazole, and WO 99/64415 and WO 01/83475 for the preparation of compounds where $R^4$ is a ring.

In certain cases, as for example in the case of compounds of formula Ic, the compounds of formula I can be directly obtained as a salt. Alternatively, the salts of compounds of formula I can be prepared by conventional methods by treatment of a compound of formulas with a sufficient amount of a base such as for example sodium hydroxide, potassium hydroxide, calcium hydroxide or calcium carbonate. In the case of compounds of formula I which may contain basic nitrogen(s), salts thereof can also be obtained by treatment with an acid such as for example hydrochloric acid, sulfuric acid, nitric acid, oxalic acid or methanesulfonic acid. In addition, the salts of compounds of formula I can be transformed into other salts of compounds of formula I by ion exchange using an ion exchange resin.

As mentioned above, the compounds of the present invention act by inhibiting the cyclooxygenase-2 enzyme (COX-2). Therefore, they are useful for the treatment or prevention of inflammation, pain and/or fever associated with a wide range of diseases or pathologies. Thus, the compounds of the present invention are useful for the treatment or prevention of, among others, pain resulting from surgery or dental surgery; low back and neck pain; headache; toothache; pain associated with cancer, neuralgia; arthritis, including rheumatoid arthritis and juvenile arthritis; degenerative joint diseases, including osteoarthritis; gout; ankylosing spondylitis; tendinitis; pain and/or inflammation associated with traumatisms such as sprains, strains and other similar injuries, such as those produced during sport performance; synovitis; myositis; dysmenorrhea; inflammatory bowel disease (including ulcerative colitis and Crohn's disease); ocular inflammatory diseases, including conjunctivitis and endophthalmitis; corneal transplants; skin inflammatory diseases, including psoriasis, burns, eczema and dermatitis; systemic inflammatory processes, including sepsis and pancreatitis; bursitis; lupus erythematosus; common cold; rheumatic fever; and symptoms associated with influenza or other viral infections.

The compounds of the present invention can also be useful for the treatment of other pathologies mediated by COX-2. For example, the compounds of formula I can inhibit cell proliferation and consequently they can be useful for the treatment or prevention of preneoplasic disorders such as familial adenomatous polyposis as well as for the treatment or prevention of cancer, especially those cancers that produce prostaglandins or that express cyclooxygenase. The compounds of the invention can be useful for the treatment for example of liver, bladder, pancreas, ovary, prostate, cervix, lung, breast and skin cancer, and especially gastrointestinal cancers such as colon cancer.

The compounds of the present invention can also inhibit prostanoid-induced smooth muscle contraction and thus may also be useful for the prevention of preterm labour, and for the prevention or treatment of asthma and bronchitis. Other uses of the compounds of formula I include the treatment or prevention of cerebral infarction, epilepsy, type I diabetes and neurodegenerative diseases such as Parkinson's disease, amyotrophic lateral sclerosis and dementia, including Alzheimer's disease, as well as the treatment or prevention of vascular diseases with an inflammatory component such as atherosclerosis.

Moreover, the compounds of the present invention may also be used for treating inflammation in diseases such as migraine, periarteritis nodosa, thyroiditis, aplastic anaemia, Hodgkin's disease, scleroderma, myasthenia gravis, sarcoidosis, nephrotic syndrome, Behçet's syndrome, polymyositis, hypersensitivity and gingivitis.

Besides being useful for human therapy, the compounds of the invention are also useful for veterinary therapy, e.g. of companion animals, exotic animals and farm animals.

According to the activity of the products herein described, the present invention also relates to compositions which contain a compound of the present invention, together with one or more excipients or other auxiliary agents if necessary. The compounds of the present invention can be administered in the form of any pharmaceutical formulation, the nature of which, as it is well known, will depend upon the nature of the active compound and its route of administration. The compounds of the present invention are useful to be administered by any route of administration, for example by oral, topical, ocular or parenteral route. However, given their good solubility, the compounds of the invention are particularly suitable to be administered by parenteral route.

Injectable preparations of the compounds of the present invention for their parenteral administration comprise sterile solutions, suspensions or emulsions, in an aqueous or non-aqueous solvent such as propylene glycol, polyethylene glycol or vegetable oils. These compositions can also contain coadjuvants, such as wetting, preserving, emulsifying and dispersing agents. They may be sterilized by any known method or prepared as sterile solid compositions which will be dissolved in water or any other sterile injectable medium immediately before use. It is also possible to start from sterile materials and keep them under these conditions throughout all the manufacturing process.

Solid compositions for oral administration include tablets, granulates and capsules. In any case the manufacturing method is based on a simple mixture, dry granulation or wet granulation of the active compound with excipients. These excipients can be, for example, diluents such as lactose, microcrystalline cellulose, mannitol or calcium hydrogen-phosphate; binding agents such as for example starch, gelatin or polyvinylpyrrolidone; disintegrants such as sodium carboxymethyl starch or sodium croscarmellose; and lubricating agents such as for example magnesium stearate, stearic acid or talc. Tablets can be additionally coated with suitable excipients by using known techniques with the purpose of delaying their disintegration and absorption in the gastrointestinal tract and thereby provide a sustained action over a longer period, or simply to improve their organoleptic properties or their stability. The active compound can also be incorporated by coating onto inert pellets using natural or synthetic film-coating agents. Soft gelatin capsules are also possible, in which the active compound is mixed with water or an oily medium, for example coconut oil, liquid, paraffin or olive oil.

Powders and granulates for the preparation of oral suspensions by the addition of water can be obtained by mixing the active compound with dispersing or welting agents; suspending agents and preservatives. Other excipients can also be added, for example sweetening, flavouring and colouring agents.

Liquid forms for oral administration include emulsions, solutions, suspensions, syrups and elixirs containing commonly-used inert diluents, such as distilled water, ethanol, sorbitol, glycerol, polyethylene glycols and propylene glycol. Said compositions can also contain coadjuvants such as wetting, suspending, sweetening, flavouring, preserving agents and buffers.

A compound of the invention can also be formulated for its topical application for the treatment of pathologies occurring in areas or organs accessible through this route, such as eyes, skin and the intestinal tract. Formulations include creams, lotions, gels, powders, solutions and patches wherein the compound is dispersed or dissolved in suitable excipients.

The activity of the compounds of the present invention can be determined using the following tests:

Test 1.—Rat Carrageenan-Induced Paw Edema Assay

Male Sprague Dawley rats (150-175 g) are used. The animals are fasted during 18 hours prior to the experiment and kept with water ad libitum, and are randomly distributed into the different groups of treatment. Inflammation is induced by injecting 0.1 mL of 1% λ-carrageenan solution (Sigma) to the animals' right hindpaw, and the inflammatory response (increase in paw volume) is measured with a plethysmometer (UGO BASILE). Paw volumes are measured just before the administration of test compounds and at 1, 2, 3 and 4 hours after the injection of carrageenan. The compounds are administered through the tail vein, dissolved in DMSO and saline (1 mL/Kg), 10 minutes before the injection of carrageenan. At the same time, 5 mL of water are administered by the oral route in order to facilitate hydration and subsequent inflammatory reaction. The percentages of inhibition of the different treatments tested are calculated by comparing the area under the curve obtained for the treated animals versus the one obtained for the control group. Said areas are obtained by integration from a graphical representation of paw volume versus time.

The results obtained with representative compounds of the present invention are shown in the following table, where the % of inhibition of inflammation at a dose of 3 mg/kg i.v. of test compound are reported.

| No. Example | % inhibition (3 mg/kg) |
|---|---|
| 1 | 20.7 |
| 4 | 23.3 |
| 6 | 34.8 |

The compounds of the invention can also be evaluated in this model when administered by the oral route.

Test 2.—Air Pouch Model of Inflammation in the Rat

This model allows to evaluate COX-2 inhibition in vivo. Male Lewis rats (175-200 g), randomly distributed into the different groups of treatment, are used. Air cavities (pouches) are produced to each group by subcutaneous and interscapular injection of 20 mL of sterile air. To keep the air pouch open, 10 mL of air is further administered to each group every two days. Seven days after the first air injection, 2 mL of 1% λ-carrageenan solution (Sigma) is administered to each group into the air pouch to produce an inflammatory reaction. The test compound is administered orally 30 min before the carrageenan injection. Animals are killed 6 hours later and the exudate volume is measured. The exudate is centrifuged at 1200×g at 4° C. for 5 min, and the $PGE_2$ concentration in the supernatant is determined by using a specific enzymatic immunoassay technique.

The compounds of the invention can also be evaluated in this model when administered by the intravenous route.

Test 3.—Rat Carrageenan-Induced Hyperalgesia Test

Male Sprague Dawley rats, randomly distributed into the different groups of treatment, are used. Inflammation is induced by injection of a carrageenan suspension (0.75 mg per paw in 0.05 mL of saline) into the animals' right hind foot pad. One hour 45 min later the test compounds are administered by intravenous route. Two hours after carrageenan injection, hyperalgesia is induced at different times in both hindpaws by using a heat source. At each time, the time of latency till the withdrawal of the paw from the heat source is determined for the control group (vehicle) and the treatment groups, and the result is expressed as the increase of the latency time of the inflammed paw of the treated group versus the control group.

The compound of example 6 administered at a dose of 3 mg/Kg showed a significant analgesic activity in this model, especially at 120 min after administration.

The following examples illustrate, but do not limit, the scope of the present invention. The following abbreviations have been used in the examples:
ACN: acetonitrile
EtOAc: ethyl acetate
AcOH: acetic acid
EtOH: ethanol
MeOH: methanol
Pr'OH: isopropanol
THF: tetrahydrofuran Example 1

Diethyl N-[4-[4-chloro-5-(3-fluoro methoxyphenyl) imidazol-1-yl]phenylsulfonyl]phosphoramidate To a solution of 4-[4-chloro-5-(3-fluoro-4-methoxyphenyl)imidazol-1-yl]benzenesulfonamide (2 g, 5.2 mmol) (obtained as described in WO 00/23426) in 1N NaOH (7.2 mL) (pH 13.4) under argon atmosphere, a solution of diethyl chlorophosphate (5.2 mL, 36.4 mmol) in THF (28 mL) was added dropwise over 5 min. In order to keep the reaction mixture soluble during all the addition process, some drops of 2N NaOH were added each time the reaction mixture became turbid. Once the addition was finished (pH 8), the resulting mixture was stirred at room temperature for 1 h, treated with EtOAc and the phases were separated. The organic phase was extracted with a NaOH solution having pH 7-8, the phases were separated and the extracted aqueous phase, combined with the previous one, was brought to pH 4 and extracted with EtOAc. The extracted organic phase was dried over $Na_2SO_4$ and concentrated to dryness, to afford 2 g of the title compound of the example (74% yield).

$^1$H-NMR (300 MHz, $CDCl_3$ δ TMS): 1.29 (t, J=7.1 Hz, 6H), 2.0 (broad signal, $H_2O+NH$), 3.90 (s, 3H), 4.12 (m, 4H), 6.93 (m, 3H), 7.23 (d, J=8.7 Hz, 2H), 7.63 (s, 1H), 8.02 (d, J=8.7 Hz, 2H).

Elemental analysis calculated for $C_{20}H_{22}ClN_3O_6PS$: C 46.38%; H 4.28%; N 8.11%. Found: C 46.54%; H 4.37%; N 7.82%.

Example 2

Diethyl N-[4-[4-chloro-5-(3-fluoro-4-methoxyphenyl)imidazol-1-yl]phenylsulfonyl]phosphoramidate Sodium Salt To a suspension of diethyl N-[4-[4-chloro-5-(3-fluoro-4-methoxyphenyl)imidazol-1-yl]phenylsulfonyl]phosphoramidate (1 g, 1.9 mmol) (obtained in example 1) in EtOH (35 mL), NaOH powder (76 mg, 1.9 mmol) in EtOH (4 mL) was added, and the resulting mixture was stirred under argon atmosphere and at room temperature for 1 h. The mixture was concentrated to dryness and the resulting solid was recrystallized from Pr$^i$OH (20 mL), to afford the title compound of the example as a white solid (0.88 g; 86% yield).

Elemental analysis calculated for $C_{20}H_{21}ClFN_3NaO_6PS.0.5H_2O$: C 43.76%; H 4.01%; N 7.65%. Found: C 43.72%; H 3.63%; N 7.58%.

Example 3

Diethyl N-[4-[4-chloro-S-(3-fluoro-4-methoxyphenyl)imidazol-1-yl]phenylsulfonyl]phosphoramidate Potassium Salt Following a similar procedure to that described in example 2, but using KOH instead of NaOH, the title compound of the example was obtained as a white solid (48% yield).

Elemental analysis calculated for $C_{20}H_{21}ClFKN_3O_6PS.0.5H_2O$: C 42.51%; H 4.04%; N 7.43%. Found: C 42.40%; H 3.65%; N 7.35%.

Example 4

Ethyl N-[4-[4-chloro-5-(3-fluoro-4-methoxyphenyl)imidazol-1-*yl]phenylsulfonyl]phosphoramidate Sodium Salt To a suspension of diethyl N-[4-[4-chloro-5-(3-fluoro-4-methoxyphenyl)imidazol-1-yl]phenylsulfonyl]phosphoramidate (1 g, 1.9 mmol) (obtained in example 1) in acetone (14 mL) under argon, NaI (284 mg, 1.9 mmol) was added, and the resulting mixture was stirred at reflux overnight. It was concentrated to dryness and the crude product obtained was purified by chromatography on silica gel using EtOAc/MeOH/AcOH mixtures of increasing polarity as eluent. The product obtained was next recrystallized from Pr$^i$OH to afford 554 mg of the title compound of the example (57% yield).

$^1$H-NMR (300 MHz, $CDCl_3+CD_3OD$ δ TMS): 1.20 (m, 3H), 3.74 (m, 2H), 3.90 (s, 3H), 4.30 (s, $H_2O+NH$), 6.95 (m, 3H), 7.29 (d, J=7.7 Hz, 2H), 7.74 (s, 1H), 8.06 (d, J=7.7 Hz, 2H).

Elemental analysis calculated for $C_{18}H_{17}ClFN_3NaO_6PS.0.5H_2O$: C 41.50%; H 3.46%; N 8.06%. Found: C 41.31%; H 3.71%; N 7.27%.

Example 5

Ethyl N-[4-[4-chloro-5-(3-fluoro-4-methoxyphenyl)imidazol-1-yl]phenylsulfonyl]phosphoramidate Potassium Salt Following a similar procedure to that described in example 4, but using potassium iodide instead of sodium iodide, the title compound of the example was obtained in 29% yield.

$^1$H-NMR (300 MHz, $CDCl_3+CD_3OD$ δ TMS): 1.11 (m, 3H), 3.71 (m, 2H), 3.85 (s, 3H), 4.15 (s, $H_2O+NH$), 6.90 (m, 3H), 7.23 (d, J=8.6 Hz, 2H), 7.68 (s, 1H), 8.00 (d, J=8.6 Hz, 2H).

Elemental analysis calculated for $C_{18}H_{17}ClFKN_3O_6PS.1H_2O$: C 39.60%; H 3.48%; N 7.69%. Found: C 39.40%; H 3.27%; N 7.56%.

Example 6

N-[4-[4-Chloro-5-(3-fluoro-4-methoxyphenyl)imidazol-1-yl]phenylsulfonyl]phosphoramidic Acid Method A To a suspension of diethyl N-[4-[4-chloro-5-(3-fluoro-4-methoxyphenyl)imidazol-1-yl]phenylsulfonyl]phosphoramidate (1 g, 1.92 mmol) (obtained in example 1) in $CH_2Cl_2$ (22 mL), cooled to 0° C. and under argon atmosphere, iodotrimethylsilane (1.3 mL, 9.6 mmol) was added dropwise, and the resulting mixture was stirred at 0° C. for 1 h. Then, the mixture was concentrated to dryness and the residue obtained was treated with a mixture of acetone (22 mL) and $H_2O$ (0.76 mL). The resulting mixture was first stirred at 0° C. for 1 h and then at room temperature overnight. A solid precipitated, which was collected by filtration, washed with acetone and dried. The title compound of the example was obtained in 80% yield (0.7 g).

Method B

To a suspension of diethyl N-[4-[4-chloro-5-(3-fluoro-4-methoxyphenyl)imidazol-1-yl]phenylsulfonyl]phosphoramidate (0.12 g, 0.23 mmol) (obtained in example 1) in ACN (1 mL), bromotrimethylsilane (0.3 mL, 2.3 mmol) was added dropwise and under argon atmosphere, and the resulting mixture was stirred at room temperature overnight. The mixture was concentrated to dryness and the residue obtained was dried and then stirred in $H_2O$ (0.167 mL) for 1 h. EtOH (1.67 mL) was added and the mixture was further stirred for half an hour and was then kept overnight at 4° C. A solid precipitated, which was collected by filtration and dried, affording 65 mg of the title compound of the example (61% yield).

$^1$H-NMR (300 MHz, $CDCl_3+CD_3OD$ δ TMS): 3.91 (s, 3H), 4.46 (s, $H_2O+3H$), 6.95 (m, 3H), 7.31 (d, J=8.7 Hz, 2H), 7.78 (s, 1H), 8.04 (d, J=8.7 Hz, 2H).

Elemental analysis calculated for $C_{16}H_{14}ClFN_3O_6PS$: C 41.61%; H 3.06%; N 9.10%. Found: C 41.22%; H 2.75%; N 9.20%.

Example 7

Trisodium N-[4-[4-chloro-5-(3-fluoro-4-methoxyphenyl)imidazol-1-yl]phenylsulfonyl]phosphoramidate Following a similar procedure to that described in example 2, but using N-[4-[4-chloro-5-(3-fluoro-4-methoxyphenyl)imidazol-1-yl]phenylsulfonyl]-phosphoramidic acid (obtained in example 6) instead of diethyl N-[4-[4-chloro-5-(3-fluoro-4-methoxyphenyl)imidazol-1-yl]phenylsulfonyl] phosphoramidate and 3 equivalents of NaOH instead of 1, and recrystallizing then the crude product obtained from Pr$^i$OH, the title compound of the example was obtained as a white solid.

Elemental analysis calculated for $C_{16}H_{11}ClFN_3Na_3O_6PS.2H_2O$: C 34.10%; H 2.65%; N 7.45%. Found: C 33.91%; H 2.25%; N 6.90%.

Example 8

Tripotassium N-[4-[4-chloro-5-(3-fluoro-4-methoxyphenyl)imidazol-1-yl]phenylsulfonyl]phosphoramidate Following a similar procedure to that described in example 7, but using 3 equivalents of KOH instead of 3 equivalents of NaOH, and recrystallizing the crude product obtained from EtOH, the title compound of the example was obtained as a white solid.

Elemental analysis calculated for $C_{16}H_{11}ClFK_3N_3O_6PS.H_2O$: C 32.32%; H 2.19%; N 7.07%. Found: C 32.06%; H 2.09%; N 6.62%.

Example 9

Dipotassium N-[4-[4-chloro-5-(3-fluoro-4-methoxyphenyl)imidazol-1-yl]phenylsulfonyl]phosphoramidate Following a similar procedure to that described in example 8, but using 2 equivalents of KOH instead of 3, and recrystallizing the crude product obtained from EtOH, the title compound of the example was obtained as a white solid.

Elemental analysis calculated for $C_{16}H_{12}ClFK_2N_3O_6PS.H_2O$: C 34.56%; H 2.52%; N 7.55%; S 5.76%. Found: C 34.22%; H 2.31%; N 7.35%; S 5.52%.

Example 10

Calcium N-[4-[4-chloro-5-(3-fluoro-4-methoxyphenyl)imidazol-1-yl]phenylsulfonyl]phosphoramidate A suspension of N-[4-[4-chloro-5-(3-fluoro-4-methoxyphenyl)imidazol-1-yl]phenylsulfonyl]phosphoramidic acid (0.3 g, 0.65 mmol) (obtained in example 6) and $CaCO_3$ (66 mg, 0.66 mmol) in $H_2O$ (38 mL) was stirred at room temperature for 1 h. A white solid was formed, which was collected by filtration, washed with $H_2O$ and dried, to afford the title compound of the example in 71% yield.

Elemental analysis calculated for $C_{16}H_{12}CaClFN_3O_6PS.2.5H_2O$: C 35.13%; H 3.11%; N 7.68%. Found: C 34.82%; H 3.43%; N 7.17%.

Example 11

Tricalcium di-[N-[4-[4-chloro-5-(3-fluoro-4-methoxyphenyl)imidazol-1-yl]phenylsulfonyl]phosphoramidate]

Following a similar procedure to that described in example 7, but using 1.5 equivalents of $Ca(OH)_2$ instead of 3 equivalents of NaOH, and recrystallizing the crude product obtained from EtOH, the title compound of the example was obtained as a white solid (85% yield).

Elemental analysis calculated for $C_{32}H_{22}Ca_3Cl_2F_2N_6O_{12}P_2S_2$: C 32.35%; H 2.21%; N 7.07%. Found: C 32.27%; H 2.40%; N 6.85%.

Example 12

Diethyl N-[4-[4-chloro-5-(4-ethoxyphenyl)imidazol-1-yl]phenylsulfonyl]phosphoramidate a) 4-[4-Chloro-5-(4-ethoxyphenyl)imidazol-1-yl] benzenesulfonamide Sodium Salt To a suspension of 4-[4-chloro-5-(4-ethoxyphenyl)imidazol-1-yl]benzenesulfonamide (1 g, 2.89 mmol) (obtained as described in WO 00/23426) in EtOH (55 mL), NaOH powder (115 mg, 2.89 mmol) was added under argon atmosphere, and the resulting mixture was stirred at room temperature for 2 h. The mixture was concentrated to dryness and a crude product was obtained, which was directly used in the following reaction.

b) Title Compound

To a suspension of 4-[4-chloro-5-(4-ethoxyphenyl)imidazol-1-yl]benzenesulfonamide sodium salt (2.89 mmol) (obtained in the preceding section) in THF (12 mL), diethyl chlorophosphate (0.42 mL, 2.89 mmol) was added under argon atmosphere. The resulting solution was stirred at room temperature for 15 days. It was then concentrated to dryness and the resulting residue was partitioned between $H_2O$ and EtOAc, the suspension was filtered and the phases separated. The organic phase was dried and concentrated to afford a solid which was purified by chromatography on silica gel using mixtures hexane/EtOAc and EtOAc/MeOH of increasing polarity as eluent. The product obtained was then recrystallized from ACN to afford the title compound of the example as a yellowish solid (15% yield).

$^1$H-NMR (300 MHz, CDCl$_3$ δ TMS): 1.34 (t, J=7.1 Hz, 6H), 1.47 (t, J=7.0 Hz, 3H), 2.0 (broad signal, NH), 4.08 (q, J=7.0 Hz, 2H), 4.17 (m, 4H), 6.90 (d, J=8.8 Hz, 2H), 7.15 (d, J=8.8 Hz, 2H), 7.31 (d, J=8.7 Hz, 2H), 7.69 (s, 1H), 8.04 (d, J=8.7 Hz, 2H).

Elemental analysis calculated for $C_{21}H_{25}ClN_3O_6PS.0.25H_2O$: C 48.65%; H 5.01%; N 8.10%. Found: C 48.59%; H 4.89%; N 8.08%.

Example 13

N-[4-[4-Chloro-5-(4-ethoxyphenyl)imidazol-1-yl] phenylsulfonyl]phosphoramidic Acid Following a similar procedure to that described in method A of example 6, but starting from diethyl N-[4-[4-chloro-5-(4-ethoxyphenyl)imidazol-1-yl]phenylsulfonyl]phosphoramidate (obtained in example 12) instead of diethyl N-[4-[4-chloro-5-(3-fluoro-4-methoxyphenyl)imidazol-1-yl]

phenylsulfonyl]-phosphoramidate, the title compound of the example was obtained in 63% yield.

¹H-NMR (300 MHz, CDCl₃+CD₃OD δ TMS): 1.37 (t, J=7.0 Hz, 3H), 4.00 (q, J=7.0, 2H), 4.30 (s, H₂O+3H), 6.82 (d, J=8.7 Hz, 2H), 7.07 (d, J=8.7 Hz, 2H), 7.25 (d, J=8.5 Hz, 2H), 7.72 (s, 1H), 7.97 (d, J=8.5 Hz, 2H).

Elemental analysis calculated for C₁₇H₁₇ClN₃O₆PS.0.25H₂O: C 44.16%; H 3.79%; N 9.08%. Found: C 44.17%; H 3.65%; N 9.10%.

Example 14

Diphenyl N-[4-[4-chloro-5-(3-fluoro-4-methoxyphenyl)imidazol-1-yl]phenylsulfonyl]phosphoramidate Following a similar procedure to that described in sections a and b of example 12, but using 4-[4-chloro-5-(3-fluoro-4-methoxyphenyl)imidazol-1-yl]benzenesulfonamide (obtained as described in WO 00/23426) instead of 4-[4-chloro-5-(4-ethoxyphenyl)imidazol-1-yl]benzenesulfonamide and diphenyl chlorophosphate instead of diethyl chlorophosphate, the title compound of the example was obtained in 10% yield.

¹H-NMR (300 MHz, CDCl₃ δ TMS): 2.0 (broad signal, NH), 3.94 (s, 3H), from 6.88 to 7.11 (m, 16H), 7.93 (d, J=7.4 Hz, 2H).

Elemental analysis calculated for C₂₈H₂₂ClFN₃O₆PS.H₂O: C 51.15%; H 3.83%; N 6.65%. Found: C 51.15%; H 3.46%; N 5.92%.

Example 15

Diphenyl N-[4-[4-Chloro-5-(3-fluoro-4-methoxyphenyl)imidazol-1-yl]phenylsulfonyl]phosphoramidate Sodium Salt Following a similar procedure to that described in example 2, but starting from diphenyl N-[4-[4-chloro-5-(3-fluoro-4-methoxyphenyl)imidazol-1-yl]phenylsulfonyl]phosphoramidate (obtained in example 14) instead of diethyl N-[4-[4-chloro-5-(3-fluoro-4-methoxyphenyl)imidazol-1-yl] phenylsulfonyl]-phosphoramidate and without recrystallizing the crude product obtained, the title compound of the example was obtained in quantitative yield.

Elemental analysis calculated for C₂₈H₂₁ClFN₃NaO₆PS.3.5H₂O: C 47.98%; H 4.05%; N 5.89%. Found: C 47.98%; H 3.38%; N 5.49%.

Example 16

Dimethyl N-[4-[4-chloro-5-(3-fluoro-4 ethoxyphenyl)imidazol-1-yl]phenylsulfonyl]phosphoramidate Following a similar procedure to that described in example 1, but using dimethyl chlorophosphate instead of diethyl chlorophosphate and recrystallizing the crude product obtained from Pr^iOH, the title compound of the example was obtained as a white solid.

¹H-NMR (300 MHz, CDCl₃ δ TMS): 2.0 (broad signal, H₂O+NH), 3.78 (s, 3H), 3.81 (s, 3H), 3.95 (s, 3H), 6.95 (m, 3H), 7.32 (d, J=8.7 Hz, 2H), 7.70 (s, 1H), 8.07 (d, J=8.7 Hz, 2H).

Elemental analysis calculated for C₁₈H₁₈ClFN₃O₆PS.0.5H₂O: C 43.33%; H 3.81%; N 8.42%. Found: C 43.62%; H 3.66%; N 8.13%.

Example 17

Dimethyl N-[4-[4-chloro-5-(3-fluoro-4-methoxyphenyl)imidazol-1-yl]phenylsulfonyl]phosphoramidate Sodium Salt Following a similar procedure to that described in example 2, but starting from dimethyl N-[4-[4-chloro-5-(3-fluoro-4-methoxyphenyl)imidazol-1-yl]phenylsulfonyl]phosphoramidate (obtained in example 16) instead of diethyl N-[4-[4-chloro-5-(3-fluoro-4-methoxyphenyl)imidazol-1-yl] phenylsulfonyl]-phosphoramidate, the title compound of the example was obtained as a white solid (45% yield).

Elemental analysis calculated for C₁₈H₁₇ClFN₃NaO₆PS.1H₂O: C 40.79%; H 3.59%; N 7.93%. Found: C 40.96%; H 3.72%; N 7.57%.

Example 18

Dimethyl N-[4-[4-chloro-5-(3-fluoro-4-methoxyphenyl)imidazol-1-yl]phenylsulfonyl]phosphoramidate Potassium Salt Following a similar procedure to that described in example 17, but using KOH instead of NaOH, the title compound of the example was obtained as a white solid (79% yield).

Elemental analysis calculated for C₁₈H₁₇ClFKN₃O₆PS: C 40.95%; H 3.25%; N 7.96%. Found: C 41.24%; H 3.15%; N 7.95%.

Example 19

Methyl N-[4-[4-chloro-5-(3-fluoro-4-methoxyphenyl)imidazol-1-yl]phenylsulfonyl]phosphoramidate Sodium Salt Following a similar procedure to that described in example 4 but starting from dimethyl N-[4-[4-chloro-5-(3-fluoro-4-methoxyphenyl)imidazol-1-yl]phenylsulfony]phosphoramidate instead of diethyl N-[4-[4-chloro-5-(3-fluoro-4-methoxyphenyl)imidazol-1-yl]phenylsulfony]phosphoramidate, the title compound of the example was obtained as a white solid (79% yield).

¹H-NMR (300 MHz, CDCl₃+CD₃OD δ TMS): 3.33 (m, 3H), 4.36 (s, H₂O+NH), 3.85 (s, 3H), 6.95 (m, 3H), 7.24 (d, J=7.7 Hz, 2H), 7.72 (s, 1H), 8.01 (d, J=7.7 Hz, 2H).

Elemental analysis calculated for C₁₇H₁₅ClFN₃NaO₆PS.0.4Pr^iOH: C 41.88%; H 3.50%; N 8.05%. Found: C 41.88%; H 3.64%; N 7.83%.

Example 20

Diethyl N-[4-[5-(p-tolyl)-3-(trifluoromethyl)pyrazol-1-yl]phenylsulfonyl]phosphoramidate Following a similar procedure to that described in sections a and b of example 12, but starting from 4-[5-(p-tolyl)-3-(trifluoromethyl)pyrazol-1-yl]benzenesulfonamide (obtained as described in WO 95/15316) instead of 4-[4-chloro-5-(4-ethoxyphenyl)imidazol-1-yl]benzenesulfonamide, and washing the product thus obtained with diethyl ether instead of recrystallizing it from ACN, the title compound of the example was obtained as a yellowish solid.

¹H-NMR (300 MHz, CDCl₃ δ TMS): 1.16 (t, J=7.1 Hz, 6H), 2, 0 (broad signal, NH), 2.34 (s, 3H), 3.95 (m, 4H), 6.70

Example 21

N-[4-[5-(p-Tolyl)-3-(trifluoromethyl)pyrazol-1-yl]phenylsulfonyl]phosphoramidic Acid Following a similar procedure to that described in method A of example 6 but starting from diethyl N-[4-[5-(p-tolyl)-3-(trifluoromethyl)pyrazol-1-yl]phenylsulfonyl]phosphoramidate instead of diethyl N-[4-[4-chloro-5-(3-fluoro-4-methoxyphenyl)imidazol-1-yl]phenylsulfonyl]phosphoramidate, the title compound of the example is obtained.

Example 22

Diethyl N-[4-(5-methyl-3-phenylisoxazol-4-yl)phenylsulfonyl]phosphoramidate

Following a similar procedure to that described in sections a and b of example 12, but starting from 4-(5-methyl-3-phenylisoxazol-4-yl)benzenesulfonamide (obtained as described in WO 96/25405) instead of 4-[4-chloro-5-(4-ethoxyphenyl)imidazol-1-yl]benzenesulfonamide, and recrystallizing the product thus obtained from an EtOAc/hexane mixture instead of ACN, the title compound of the example was obtained as a yellowish solid.

$^1$H-NMR (300 MHz, CDCl$_3$ δ TMS): 1.33 (t, J=7.1 Hz, 6H), 2, 0 (broad signal, NH), 2.53 (s, 3H), 4.17 (m, 4H), 7.39 (m, 7H), 8.02 (d, J=8.4 Hz, 2H).
Elemental analysis calculated for C$_{20}$H$_{23}$N$_2$O$_6$PS.1.5H$_2$O: C 50.31%; H 5.45%; N 5.86%. Found: C 50.63%; H 5.39%; N 5.65%.

Example 23

N-[4-(5-methyl-3-phenylisoxazol-4-yl)phenylsulfonyl]phosphoramidic Acid

Following a similar procedure to that described in method A of example 6, but starting from diethyl N-[4-(5-methyl-3-phenylisoxazol-4-yl)phenylsulfonyl]phosphoramidate instead of diethyl N-[4-[4-chloro-5-(3-fluoro-4-methoxyphenyl)imidazol-1-yl]phenylsulfonyl]phosphoramidate, the title compound of the example is obtained.

Example 24

Diethyl N-[4-[4-cyclohexyl-2-methyloxazol-5-yl]-2-fluorophenylsulfonyl]phosphoramidate Following a similar procedure to that described in sections a and b of example 12, but starting from 4-[4-cyclohexyl-2-methyloxazol-5-yl]-2-fluorobenzenesulfonamide (obtained as described in EP 745596) instead of 4-[4-chloro-5-(4-ethoxyphenyl)imidazol-1-yl]benzenesulfonamide, the title compound of the example is obtained.

Example 25

N-[4-[4-Cyclohexyl-2-methyloxazol-5-yl]-2-fluorophenylsulfonyl]phosphoramidic Acid Following a similar procedure to that described in method A of example 6, but starting from diethyl N-[4-[4-cyclohexyl-2-methyloxazol-5-yl]-2-fluorophenylsulfonyl]phosphoramidate instead of diethyl N-[4-[4-chloro-5-(3-fluoro-4-methoxyphenyl)imidazol-1-yl]phenylsulfonyl]phosphoramidate, the title compound of the example is obtained.

The invention claimed is:
1. A compound of general formula I:

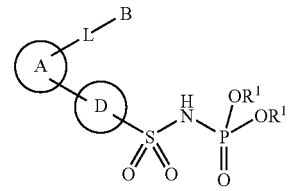

wherein:
each $R^1$ independently represents hydrogen, $C_{1-6}$ alkyl, $C_{1-6}$ haloalkyl, phenyl, heteroaryl or phenyl$C_{1-3}$ alkyl, where all phenyl and heteroaryl rings can be optionally substituted with one or more halogen, $C_{1-4}$ alkyl or $C_{1-4}$ alkoxy groups, or both substituents $R^1$ may be taken together to form a saturated or partially unsaturated 5- or 6-membered ring, which can be optionally fused to a benzene ring;

A represents an imidazole, pyrazole, isoxazole or oxazole, where the substituents L and D are placed on adjacent atoms of ring A, and where additionally A can be optionally substituted with one or more substituents $R^2$;

L represents a single bond, —O—, —S— or —NR$^3$—;

B represents $C_{1-6}$ alkyl or a ring selected from phenyl, heteroaryl and $C_{3-7}$ cycloalkyl, where all said rings can be optionally substituted with one or more substituents $R^4$;

D represents phenyl or pyridine, each of which can be optionally substituted with one or more halogens;

the groups A and —SO$_2$NHP(O)(OR$^1$)$_2$ are placed on ring D in para position with respect to one another;

each $R^2$ independently represents halogen, cyano, nitro, carboxy, $C_{1-4}$ alkyl, $C_{2-4}$ alkenyl, $C_{2-4}$ alkynyl, $C_{1-4}$ haloalkyl, hydroxy, $C_{1-4}$ hydroxyalkyl, $C_{1-4}$ alkoxy, $C_{1-4}$ haloalkoxy, $C_{1-4}$ alkylthio, amino, $C_{1-4}$ alkylamino, $C_{1-4}$ dialkylamino, formyl, $C_{1-4}$ alkylcarbonyl, $C_{1-4}$ alkoxycarbonyl, $C_{1-4}$ haloalkoxycarbonyl, $C_{1-4}$ alkoxyC$_{1-3}$ alkyl, $C_{1-4}$ alkylcarbonyloxyC$_{1-3}$ alkyl, $C_{3-7}$ cycloalkylC$_{1-4}$alkoxyC$_{1-3}$ alkyl or C$_{3-7}$ cycloalkoxyC$_{1-3}$ alkyl, or two substituents $R^2$ on the same carbon atom can be taken together to form an oxo group;

$R^3$ represents hydrogen or $C_{1-4}$ alkyl;

each $R^4$ independently represents halogen, cyano, nitro, carboxy, $C_{1-4}$ alkyl, $C_{1-4}$ haloalkyl, hydroxy, $C_{1-4}$ hydroxyalkyl, $C_{1-4}$ alkoxy, $C_{1-4}$ haloalkoxy, $C_{1-4}$ alkylthio, amino, $C_{1-4}$ alkylamino, $C_{1-4}$ dialkylamino, formyl, $C_{1-4}$ alkylcarbonyl, $C_{1-4}$ alkoxycarbonyl or C$_{1-4}$ haloalkoxycarbonyl, or two substituents $R^4$ on the same carbon atom can be taken together to form an oxo group, and additionally one of the substituents $R^4$ can represent a saturated, unsaturated or partially unsaturated 5- or 6-membered ring which can optionally contain from 1 to 3 heteroatoms selected from N, O and S and which can be optionally substituted with one or more substituents $R^5$;

each $R^5$ independently represents halogen, hydroxy, nitro, cyano, amino, $C_{1-4}$ alkyl, $C_{1-4}$ haloalkyl, $C_{1-4}$ alkoxy or $C_{1-4}$ alkylcarbonyl, or two substituents $R^5$ on the same carbon atom can be taken together to form an oxo group; and heteroaryl in the above definitions represents pyridine, pyrazine, pyrimidine or pyridazine;

or a salt thereof.

2. A compound according to claim 1 wherein A can be optionally substituted with one to four substituents $R^2$.

3. A compound according to claim 2 wherein A can be optionally substituted with one or two substituents $R^2$.

4. A compound according to claim 3 wherein A represents imidazole which can be optionally substituted with one substituent $R^2$.

5. A compound according to claim 1 wherein each $R^2$ independently represents halogen, $C_{1-4}$ alkyl or $C_{1-4}$ haloalkyl, or two substituents $R^2$ on the same carbon atom can be taken together to form an oxo group.

6. A compound according to claim 1 wherein D represents phenyl optionally substituted with a fluoro atom.

7. A compound according to claim 1 wherein L represents a single bond.

8. A compound according to claim 1 wherein B represents phenyl optionally substituted with one to three groups $R^4$ or B represents cyclohexyl.

9. A compound according to claim 1 wherein each $R^4$ independently represents halogen, $C_{1-4}$ alkyl, $C_{1-4}$ alkoxy or $C_{1-4}$ haloalkyl.

10. A compound according to claim 1 of formula Id:

Id wherein:
B represents phenyl optionally substituted with one to three groups $R^4$; and
each $R^4$ independently represents halogen, $C_{1-4}$ alkyl, $C_{1-4}$ alkoxy or $C_{1-4}$ haloalkyl.

11. A compound according to claim 10 wherein B represents 3-fluoro-4-methoxyphenyl.

12. A compound according to claim 1 wherein each $R^1$ independently represents hydrogen, $C_{1-6}$ alkyl or phenyl optionally substituted with one or more halogen, $C_{1-4}$ alkyl or $C_{1-4}$ alkoxy groups.

13. A compound according to claim 1 wherein the compound is N-[4-[4-chloro-5-(3-fluoro-4-methoxyphenyl)imidazol-1-yl]phenylsulfonyl]phosphoramidic acid, or a salt thereof.

14. A compound according to claim 13 wherein the compound is N-[4-[4-chloro-5-(3-fluoro-4-methoxyphenyl)imidazol-1-yl]phenylsulfonyl]phosphoramidic acid.

15. Process for preparing a compound of formula I according to claim 1 which comprises:
(a) when in a compound of formula I each $R^1$ is different from hydrogen, reacting a sulfonamide of formula II

II wherein A, L, B and D have the meaning described in claim 1, with a compound of formula III $$XP(O)(OR^{1a})_2$$ III wherein X represents H or Cl and wherein each $R^{1a}$ independently represents any of the meanings described for $R^1$ in claim 1 except for hydrogen, in the presence of a base, or alternatively, reacting a sulfonamide of formula II in which the group —SO$_2$NH$_2$ is in anionic form with a compound of formula III; or (b) when in a compound of formula I each $R^1$ represents hydrogen, hydrolyzing a compound of formula Ia'

Ia' wherein A, L, B and D have the meaning described in claim 1 and wherein $R^{1a'}$ represents any of the meanings described for $R^1$ in claim 1 except for hydrogen and benzyl, or alternatively, hydrogenating a compound of formula Ia"

Ia"

wherein A, L, B and D have the meaning described in claim 1; or (c) when in a compound of formula I one of the substituents $R^1$ represents hydrogen and the other is different from hydrogen, monodealkylating a compound of formula Ia'''

Ia''' wherein A, L, B, D and $R^{1a}$ have the meaning described in claim 1 and wherein $R^{1a'''}$ represents $C_{1-6}$ alkyl, $C_{1-6}$ haloalkyl or phenyl$C_{1-3}$ alkyl, where the phenyl group can be optionally substituted with one or more halogen, $C_{1-4}$ alkyl or $C_{1-4}$ alkoxy groups; or (d) transforming, in one or a plurality of steps, a compound of formula I into another compound of formula I.

16. The process of claim 15, which further comprises reacting the compound of formula I with a base or an acid to give the corresponding addition salt.

17. A pharmaceutical composition which comprises an effective amount of a compound of formula I according to claim 1 or a pharmaceutically acceptable salt thereof and one or more pharmaceutically acceptable excipients.

18. A method for the treatment of diseases mediated by cyclooxygenase-2 which comprises administering to a subject in need thereof an effective amount of a compound of formula I according to claim 1 or a pharmaceutically acceptable salt or solvate thereof, wherein the disease mediated by cyclooxygenase-2 is selected from the group consisting of: pain resulting from surgery or dental surgery; low back and neck pain; headache; toothache; pain associated with cancer; neuralgia; arthritis; degenerative joint diseases; gout; ankylosing spondylitis; tendinitis; pain or inflammation associated with sprains, strains or other traumatisms; synovitis; myositis; dysmenorrhea; inflammatory bowel disease; ocular inflammatory diseases; skin inflammatory diseases; systemic inflammatory processes; bursitis; lupus erythematosus; common cold; rheumatic fever; symptoms associated with influenza or other viral infections; asthma; bronchitis; familial adenomatous polyposis; liver cancer; bladder cancer; pancreatic cancer; ovarian cancer; prostate cancer; cervical cancer; lung cancer; breast cancer; skin cancer; gastrointestinal cancers; dementia; Parkinson's disease; amyotrophic lateral sclerosis; and atherosclerosis.

\* \* \* \* \*

UNITED STATES PATENT AND TRADEMARK OFFICE
CERTIFICATE OF CORRECTION

| | |
|---|---|
| PATENT NO. | : 7,550,497 B2 |
| APPLICATION NO. | : 10/540490 |
| DATED | : June 23, 2009 |
| INVENTOR(S) | : Rosales et al. |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (226) days Delete the phrase "by 226" and insert -- by 269 days --

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO.       : 7,550,497 B2                                Page 1 of 1
APPLICATION NO.  : 10/540490
DATED            : June 23, 2009
INVENTOR(S)      : Almansa Rosales et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this

Seventh Day of September, 2010

David J. Kappos
*Director of the United States Patent and Trademark Office*